United States Patent [19]
Flachman

[11] Patent Number: 6,009,351
[45] Date of Patent: Dec. 28, 1999

[54] SYSTEM AND METHOD FOR TRANSURETHRAL HEATING WITH RECTAL COOLING

[75] Inventor: Jonathan L. Flachman, Minneapolis, Minn.

[73] Assignee: Urologix, Inc., Minneapolis, Minn.

[21] Appl. No.: 08/892,115

[22] Filed: Jul. 14, 1997

[51] Int. Cl.⁶ .................................................. A61F 2/00
[52] U.S. Cl. ........................... 607/101; 607/102; 607/105
[58] Field of Search .................................... 607/100–105, 607/115–116, 122, 154; 606/27–33, 41–42

[56] References Cited

U.S. PATENT DOCUMENTS

| | | | |
|---|---|---|---|
| 3,125,096 | 3/1964 | Antiles et al. | 128/401 |
| 4,375,220 | 3/1983 | Matvias | 128/804 |
| 4,813,429 | 3/1989 | Eshel et al. | 128/736 |
| 5,151,100 | 9/1992 | Abele et al. | 606/28 |
| 5,197,940 | 3/1993 | Sievert et al. | |
| 5,234,004 | 8/1993 | Hascoet et al. | 607/116 |
| 5,330,518 | 7/1994 | Neilson et al. | 607/101 |
| 5,335,669 | 8/1994 | Tihon et al. | 128/736 |
| 5,344,435 | 9/1994 | Turner et al. | |
| 5,404,881 | 4/1995 | Cathaud et al. | 128/653.1 |
| 5,413,588 | 5/1995 | Rudie et al. | 607/101 |
| 5,474,071 | 12/1995 | Chapelon et al. | 128/660.03 |
| 5,484,400 | 1/1996 | Edwards et al. | 604/22 |
| 5,540,679 | 7/1996 | Fram et al. | 606/27 |

FOREIGN PATENT DOCUMENTS

| | | |
|---|---|---|
| 0 370 890 A1 | 5/1990 | European Pat. Off. |
| 0 459 535 A2 | 12/1991 | European Pat. Off. |
| 0 485 323 A1 | 5/1992 | European Pat. Off. |
| 0 519 958 B1 | 10/1994 | European Pat. Off. |
| WO 91/13650 | 9/1991 | WIPO |
| WO 91/15154 | 10/1991 | WIPO |
| WO 91/15174 | 10/1991 | WIPO |
| WO 92/15253 | 9/1992 | WIPO |
| WO 96/34571 | 11/1996 | WIPO |

OTHER PUBLICATIONS

"Histological Effects of Local Microwave Hyperthermia in Prostatic Cancer", W.L. Strohmaier et al., Int. J. Hyperthermia, 1991, vol. 7, No. 1, pp. 27–33.

*Primary Examiner*—Cary O'Connor
*Assistant Examiner*—Ryan Carter
*Attorney, Agent, or Firm*—Kinney & Lange, P.A.

[57] ABSTRACT

A system and method for treating a prostate of a patient is disclosed. The system includes a rectal probe for insertion into a rectum of the patient. A fluid supply system connected to the rectal probe supplies fluid to the rectal probe. A microwave radiation system, which is positioned anterior to the rectum of the patient, heats tumorous tissue of the prostate. The combination of the microwave radiation system and the fluid supplied to the rectal probe creates an asymmetrical heating pattern about a urethra of the patient and protects tissue adjacent to the rectal probe from thermal damage during radiation of the tumorous tissue.

18 Claims, 5 Drawing Sheets

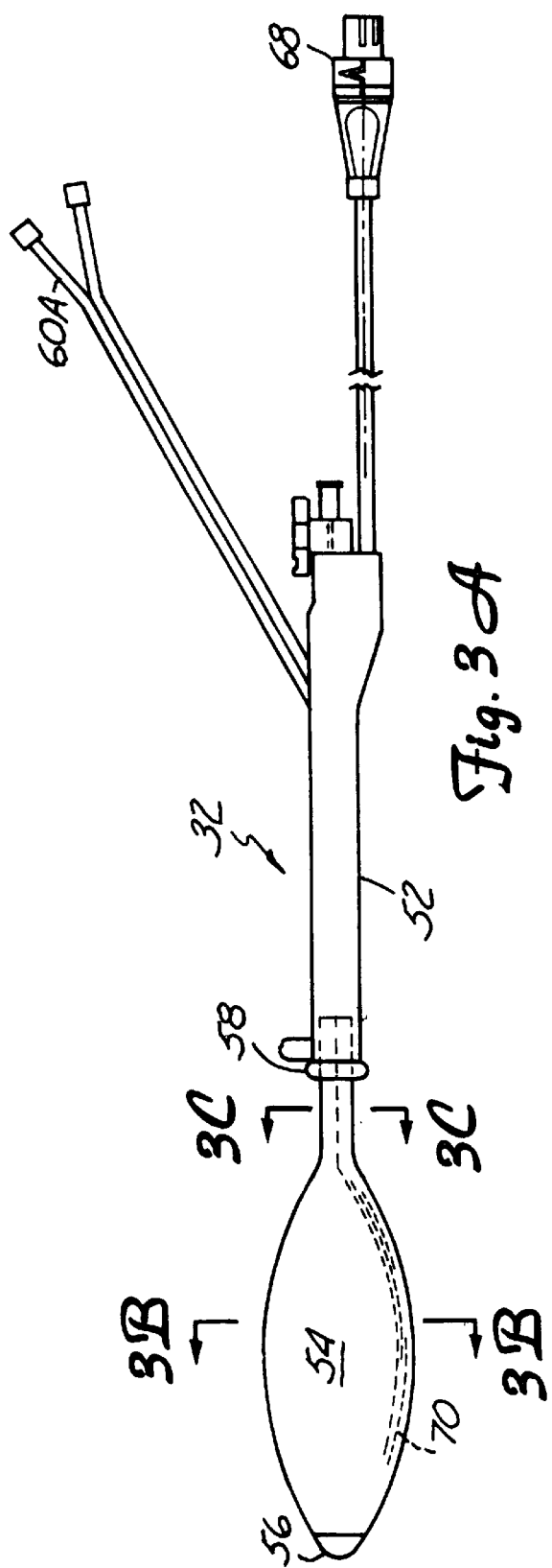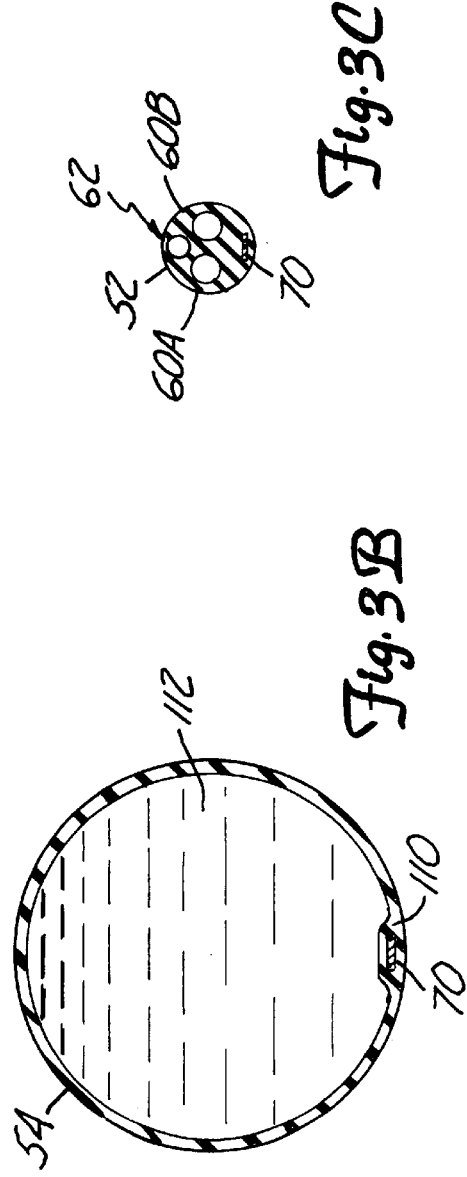
Fig. 3A
Fig. 3C
Fig. 3B

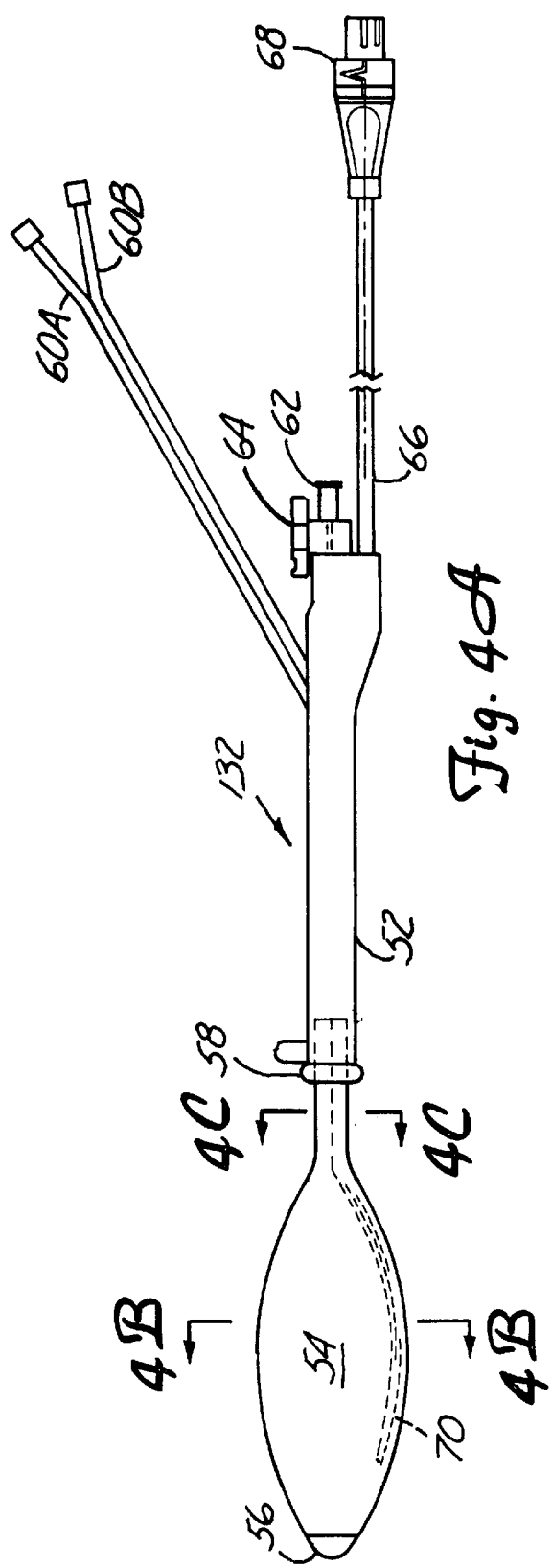
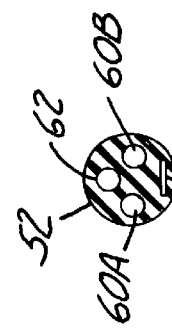
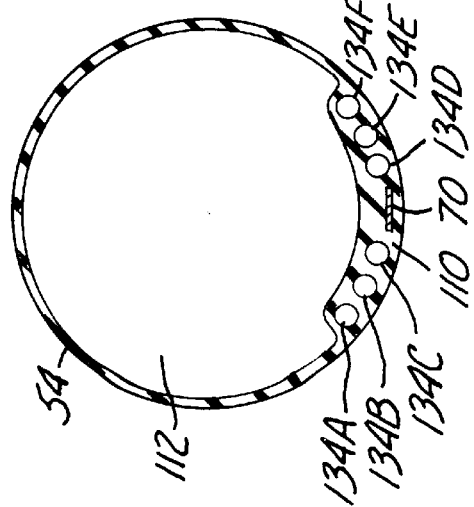

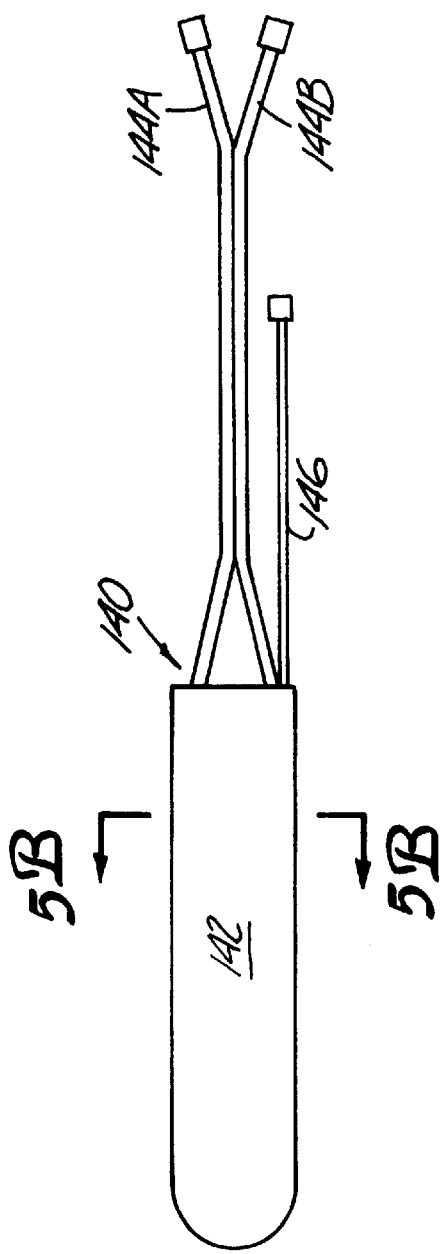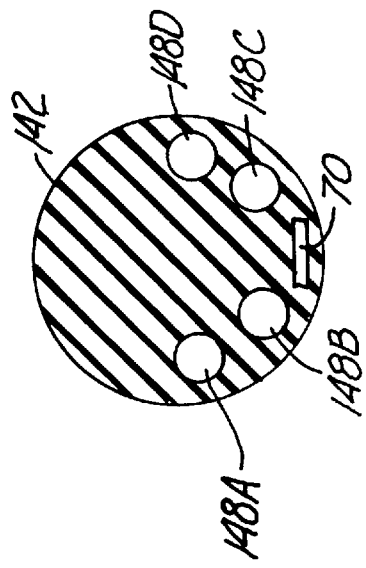
Fig. 5A
Fig. 5B

6,009,351

SYSTEM AND METHOD FOR TRANSURETHRAL HEATING WITH RECTAL COOLING

BACKGROUND OF THE INVENTION

The present invention relates to the field of microwave thermal therapy of tissue. In particular, the present invention provides rectal cooling in conjunction with heating of diseased intraprostatic tissue.

The prostate gland is a complex, chestnut-shaped organ which encircles the urethra immediately below the bladder. This relatively small organ, which is the most frequently diseased of all internal organs, is the site of a common affliction among older men: benign prostatic hyperplasia (BPH), as well as a more serious affliction, cancer. BPH is a nonmalignant, bilateral nodular expansion of the prostate tissue occurring mainly in the transition zone of the prostate. Left untreated, BPH causes obstruction of the urethra which usually results in increased urinary frequency, urgency, incontinence, nocturia and slow or interrupted urinary stream. BPH may also result in more severe complication, such as urinary tract infection, acute urinary retention, hydronephrosis and uraemia.

Recently developed treatments of BPH include transurethral microwave thermal therapy in which microwave energy is employed to elevate the temperature of diseased intraprostatic tissue surrounding the urethra above about 45° C. thereby thermally damaging the tumorous BPH tissue. Delivery of microwave energy to tumorous prostatic tissue is generally accomplished through use of a transurethral microwave antenna-containing applicator or catheter positioned within the urethra adjacent the prostate gland. The microwave antenna, when energized, heats adjacent tissue due to molecular excitation and generates a cylindrically symmetrical radiation pattern which encompasses and necroses the tumorous intraprostatic tissue. The necrosed intraprostatic tissue is subsequently reabsorbed by the body, thereby relieving an individual from the symptoms of BPH.

While transurethral microwave thermal therapy mininizes the distance between a microwave antenna-carrying applicator and the transition zone of the prostate gland, there is still concern that healthy tissue located within the radiation pattern of the microwave antenna may be thermally damaged. In particular, rectal wall and adjacent tissue may be thermally damaged during a therapy session depending upon the length of time of the therapy session and the strength of the microwave signal transmitted from the microwave antenna.

Therefore, there is a need for a system and a method which will protect rectal wall and adjacent tissue from thermal damage during a transurethral microwave thermal therapy session in which tumorous prostatic tissue is necrosed.

SUMMARY OF THE INVENTION

The present invention is a microwave thermal therapy system and method for treating a prostate of a patient. The system includes heating of diseased intraprostatic tissue in combination with rectal cooling. A rectal probe is inserted into a rectum of the patient. A fluid supply system connected to the rectal probe supplies fluid to the rectal probe. A microwave radiation system positioned anterior to the rectum of the patient heats intraprostatic tissue. The fluid supplied to the rectal probe protects tissue adjacent to the rectal probe, such as rectal wall tissue, from thermal damage. Thus, an asymmetrical heating pattern about the urethra of the patient is achieved.

BRIEF DESCRIPTION OF THE DRAWINGS

FIG. 3A is a side view of a first embodiment of a rectal probe used in the present invention.

FIGS. 3B and 3C are cross-sectional views of the rectal probe shown in FIG. 3A as viewed from lines 3B—3B and 3C—3C of FIG. 3A, respectively.

FIG. 4A is a side view of a second embodiment of a rectal probe used in the present invention.

FIGS. 4B and 4C are cross-sectional views of the rectal probe shown in FIG. 4A as viewed from lines 4B—4B and 4C—4C of FIG. 4A, respectively.

FIG. 5A is a side view of a third embodiment of a rectal probe used in the present invention.

FIG. 5B is a cross-sectional view of the rectal probe shown in FIG. 5A as viewed from lines 5B—5B of FIG. 5A.

DETAILED DESCRIPTION OF THE PREFERRED EMBODIMENTS

The present invention is a thermal therapy system and method for treatment of benign prostatic hyperplasia (BPH). The system includes heating of diseased intraprostatic tissue in combination with rectal cooling. As technology has advanced and microwave radiation protrudes deeper into the prostate, the rectum and adjacent tissue is included in the radiation pattern. With the present invention, rectal cooling prevents the temperature of rectal wall and adjacent tissue from exceeding a predetermined temperature (e.g. 42.5° C.), and thereby thermally damaging the rectal wall and adjacent tissue.

Figure 1:
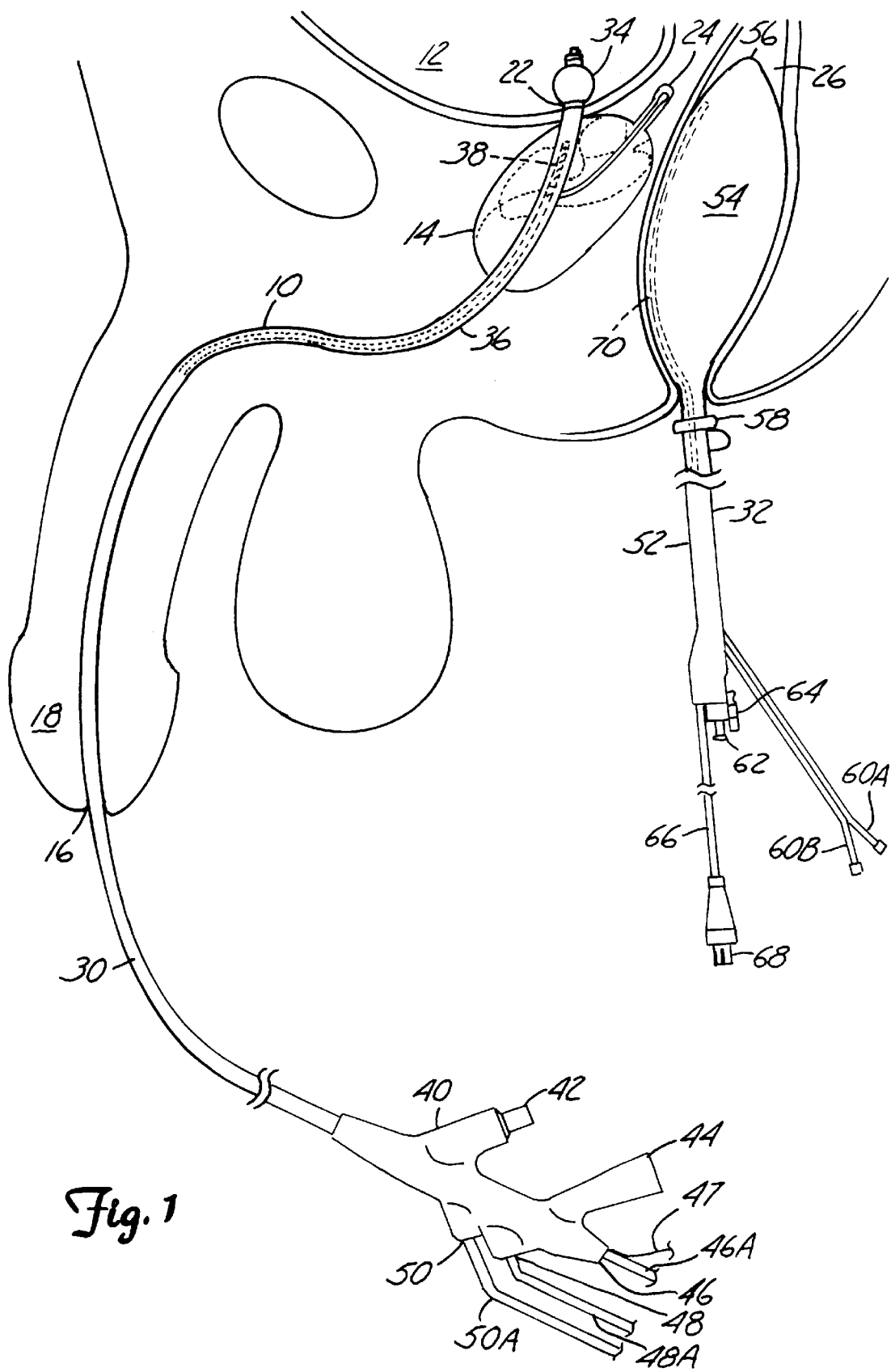
FIG. 1 is a vertical sectional view of a male pelvic region showing the present invention which includes a urethral catheter and a rectal probe positioned within a prostate region and a rectum, respectively.

FIG. 1 is a vertical sectional view of a male pelvic region showing the present invention consisting of urethral catheter 30 and rectal probe 32 positioned within urethra 10 and rectum 26, respectively. Urethra 10 is a duct leading from bladder 12, out opening 22 through prostate 14 and out orifice 16 of penis end 18. Benign tumorous tissue growth within prostate 14 around urethra 10 causes constriction of urethra 10, which interrupts the flow of urine from bladder 12 to orifice 16. The tumorous tissue of prostate 14 which encroaches urethra 10 and causes the constriction can be effectively removed by heating and necrosing the encroaching tumorous tissue. Ideally, with the present invention, periurethral tumorous tissue of prostate 14 anterior and lateral to urethra 10 is primarily heated and necrosed to avoid unnecessary and undesired damage to urethra 10 and to adjacent healthy tissues. In particular, the present invention prevents unnecessary and undesired heating and necrosing of ejaculatory duct 24 and rectum 26.

As shown in FIG. 1, urethral catheter 30 includes retention balloon 34, shaft 36, microwave antenna 38, connection manifold 40, inflation port 42, urinary drainage port 44, microwave antenna port 46, cooling fluid in port 48 and cooling fluid out port 50. Ports 42–50 communicate with corresponding lumens within shaft 36, and with lines extending from those lumens, such as microwave antenna line 46A, urethral thermometry unit cable 47, cooling fluid in port line 48A and cooling fluid out port line 50A. For example, catheter 30 preferably has the structure and features of a transurethral applicator described and illustrated in Rudie et al. U.S. Pat. No. 5,413,588. Also shown in FIG. 1, rectal probe 32 includes shaft 52, minimally distensible balloon 54 having tip 56, collar 58, fluid lines 60A and 60B, air lines 62, valve 64, electrical cable 66, electrode connection 68 and temperature sensor 70.

During a prior art therapy session to treat BPH, a therapist would have several options depending upon the specific size and location of the diseased tissue of the prostate to be treated. A first option is to utilize microwave antenna 38 within urethral catheter 30 to provide a symmetrical heating pattern about urethra 10 to necrose the diseased tissue. Urethral cooling in the form of cooling lumens within shaft 36 is provided to prevent unwanted heating of urethra 10. A second option is to utilize a microwave antenna which is positioned asymmetrically within urethral catheter 30. Such a microwave antenna will provide an asymmetric heating pattern which will encompass a larger portion of prostate 14 anterior to urethra 10. A third option is to utilize an asymmetrically positioned antenna in combination with preferential cooling lumens within shaft 36 of urethral catheter 30. The third option will provide an even greater asymmetric heating pattern anterior to urethra 10 than the second option. This method of transurethrally heating with urethral cooling with an asymmetrically positioned microwave antenna is shown and described in U.S. Pat. No. 5,413,588 entitled "DEVICE FOR ASYMMETRICAL THERMAL THERAPY WITH HELICAL DIPOLE MICROWAVE ANTENNA", which is assigned to Urologix, Inc.

During a thermal therapy session without the use of rectal cooling, energy is delivered to microwave antenna 38. Microwave antenna 38 produces a heating pattern having urethral catheter 30 in the center of the pattern. Depending upon the type of urethral catheter used, the length of the therapy session and the amount of energy supplied to microwave antenna 38, the heating pattern could encompass ejaculatory duct 24, rectum 26 and surrounding tissue. As is well known in the art, heating ejaculatory duct 24 and rectum 26 above approximately 42.5° C. must be avoided.

With the present invention, rectal probe 32 is used in conjunction with urethral catheter 30. Rectal probe 32 provides fluid to balloon 54 which will prevent the temperature of the rectal wall and surrounding tissues from increasing above a predetermined temperature. By supplying fluid to balloon 54, rectal probe 32 modifies the heating pattern caused by radiation from microwave antenna 38. In particular, the heating pattern is no longer symmetrical about urethra 10. With an asymmetrical heating pattern which does not encompass rectum 26, a greater portion of the tumorous intraprostatic tissue anterior to urethra 10 can be necrosed while healthy rectal wall and adjacent tissue posterior to urethra 10 is protected.

While using a transurethral applicator of assignee, Urologix, Inc., as shown and described in U.S. Pat. No. 5,300,099 entitled "GAMMA MATCHED HELICAL DIPOLE MICROWAVE ANTENNA" (which allows preferential heating of a prostate), is preferred to achieve the present invention, non-preferential or omni directional heating transurethral applicators such as disclosed in Hascoet et al. Pat. No. 5,234,004 can be used with rectal cooling to achieve a preferential heating pattern. In addition, the present system provides a mean for prechilling the rectal wall and adjacent tissue prior to applying microwave radiation from microwave antenna 38. The use of prechilling would permit the therapist to more quickly ramp up the power to microwave antenna 38 without damaging rectal tissue. Also, the use of prechilling and/or providing fluid to rectal probe 32 during a treatment session will provide an even greater asymmetrical heating pattern which will encompass a larger portion of prostate 14 anterior and lateral to urethra 10 without damaging ejaculatory duct 24, rectum 26 and surrounding tissue which is posterior to urethra 10.

Figure 2:
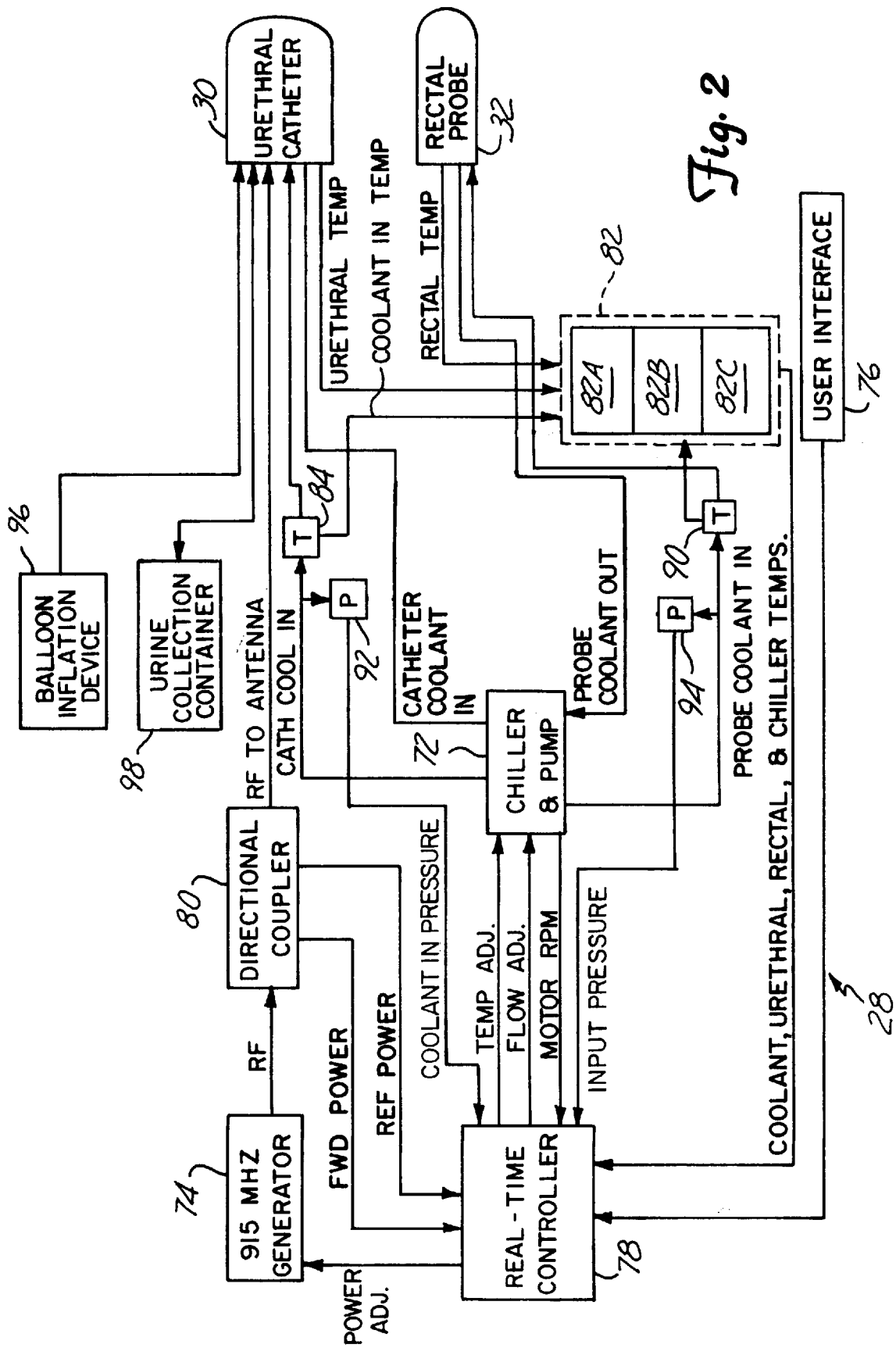
FIG. 2 is a block diagram of the transurethral microwave thermal therapy system incorporating the present invention.

FIG. 2 is a block diagram of transurethral microwave thermal therapy system 30 incorporating the present invention. System 28 includes urethral catheter 30, cooling system 72, microwave generating source 74, user interface 76, real time controller (RTC) 78, directional coupler 80, thermometry unit 82, thermometry sensors 84 and 90, coolant pressure sensors 92 and 94, balloon inflation device 96, urine collection container 98 and rectal probe 32.

As shown in FIG. 2, control of microwave generating source 74 and cooling system 72 is effected by real time controller 78, which is in turn controlled by user interface 76. User interface 76 communicates with RTC 78, which is responsible for the closed loop feedback which runs therapy system 28. In particular, RTC 78 has direct closed loop control of microwave power from microwave generating source 74, and coolant flow and coolant temperature of cooling system 76. The closed loop feedback tracks out variations in gain, drift and cable losses inherent in microwave generating source 74. The closed loop feedback also tracks the variability in pump output and refrigeration system efficiency of cooling system 72. In addition to monitoring microwave generating source 74 and cooling system 76, RTC 78 also monitors and controls several channels of thermometry via inputs from thermometry unit 82. Cooling thermometry system 82A measures the coolant and chiller temperatures based upon signals from coolant temperature sensors 84–90. Urethral thermometry system 82B measures urethral temperature based upon signals from a temperature sensor within urethral catheter 30 (not shown). Rectal thermometry system 82C measures rectal temperature based upon signals received from temperature sensor 70 within rectal probe 32. RTC 78 transmits all closed loop feedback to user interface 76, which processes the input and transmits corrections and instructions back to RTC 78. RTC 78 interprets the instructions given to it by process control language received from user interface 76 and executes the instructions in real time. All corrections from user interface 76 are made to maintain a given thermal profile throughout a thermal therapy session. In addition, system 28 includes a hardware fail-safe circuit which shuts down system 28 should any parameter fall outside a given range of values.

FIG. 3A is a side view of a first embodiment of rectal probe 32 incorporated in the present invention. FIGS. 3B–3C are cross-sectional views of rectal probe 32 shown in FIG. 3A as viewed from lines 3B—3B and 3C—3C, respectively.

Rectal probe 32 includes shaft 52, minimally distensible balloon 54 having tip 56, collar 58, fluid lines 60A and 60B, air line 62, electrical cable 66, electrical connection 68 and temperature sensor 70.

As shown in FIG. 3B, balloon 54 of rectal probe 32 is divided into two discrete areas, temperature sensor area 110 and fluid area 112. Temperature sensor 70 is positioned within temperature sensor area 110. Temperature sensor area 110 is positioned within rectal probe 32 such that when rectal probe 32 is properly inserted within the rectum of a patient, temperature sensor 70 will be located proximate to urethra 10 (shown in FIG. 1). Collar 58 ensures that rectal probe 32 is properly positioned within rectum 26.

Once rectal probe 32 is properly inserted into rectum 26, but prior to energing antenna 38, balloon 54 would be inflated with fluid lines 60A and 60B. Balloon 54 is inflated such that balloon 54 properly fills rectum 26, but does not overly distend rectum 56. Proper inflation will establish substantially complete contact with the rectal wall to prevent "hot spots" from occurring adjacent to rectal wall tissue due to over heating while also providing little or no discomfort to the patient due to improper pressure against rectum 26.

As shown in FIG. 3C, shaft 52 contains fluid lumens 60A and 60B. Fluid lumens 60A and 60B provide a path for fluid to be transmitted from cooling system 72 (shown in FIG. 2) to balloon 54 and back to cooling system 72. Thus, fluid can either be circulated within balloon 54, or fluid can simply fill balloon 54. The fluid can then be extracted from balloon 54 after treatment. Air lumen 62 permits the therapist to remove any gas from rectum 26 during a therapy session which could present undesirable pain to the patient.

The purpose of the fluid which fills balloon 54 is to maintain the temperature of the rectal wall and adjacent tissue within physiologically normal temperature ranges to prevent injury to this tissue (e.g. ejaculatory duct 24 and rectum 26) during a therapy session. Preferably, the temperature of the rectal wall and adjacent tissue is maintained below 42.5° C. Thus, it is important that balloon 54 conforms with the interior surface of rectum 26 without unnecessarily distending rectum 26. Significant distension of rectum 26 can be extremely painful to the patient.

Balloon 54 is a thermally conductive device. Balloon 54 can be made from a variety of materials as long as it remains thermally conductive. Examples of materials which can be used for balloon 54 are silicon, urethane, urethane vinyl and ADA pelethane. Balloon 54 has a preferred thickness in the range of 0.005 to 0.10 inches.

FIG. 4A is a side view of a second embodiment of a rectal probe used in the present invention. Although the exterior design of rectal probe 132 shown in FIGS. 4A–4C is similar to the exterior design of rectal probe 32 shown in FIGS. 3A–3C, the interior design of rectal probe 132 is substantially different from that of rectal probe 32. FIGS. 4B and 4C are cross sectional views of rectal probe 132 as viewed from lines 4B—4B and 4C—4C of FIG. 4A, respectively. Features of FIGS. 4A–4C which are identical to features of FIGS. 3A–3C have been labeled as such. In addition to the similar features, rectal probe 132 includes fluid lumens 134A–134F.

In the embodiment shown in FIGS. 4A–4C, balloon 54 is filled with air, rather than with fluid. Balloon inflation device 96 (shown in FIG. 2) provides air to air lumen 62 which feeds into balloon 54. Prior to therapy, balloon 54 can be expanded such that balloon 54 comes in contact with the walls of rectum 26. Fluid is delivered to lumens 60A and 60B via cooling system 72. In this embodiment, fluid lumens 60A and 60B branch out into fluid lumens 134A–134F inside of balloon 54.

Fluid lumens 134A–134F are strategically positioned within balloon 54 such that upon insertion into rectum 26 and during therapy, these lumens are proximate to urethra 10 and ejaculatory duct 24. Fluid within fluid lumens 134A–134F, which can be either circulating or stagnate, prevents the temperature of the rectal wall proximate to urethra 10 from increasing above a desired range and from being damaged due to microwave radiation. The positioning of lumens 134A–134F against the rectal wall closest to urethra 10 is necessary since the rectal wall proximate to urethra 10 will be absorbing more thermal energy than any other portion of the rectal wall during a transurethral microwave thermal therapy session. Temperature sensor 70 is utilized such that the rectal wall temperature proximate to urethra 10 can be monitored. Variations in fluid temperature and/or pressure can be used to maintain a safe temperature within rectum 26, i.e. below 42.5° C.

FIG. 5A is a side view of a third embodiment of a rectal probe used in the present invention. FIG. 5B is a cross-sectional view of the rectal probe as viewed from lines 5B—5B of FIG. 5A.

Rectal probe 140 differs from rectal probes 32 and 132 in that rectal probe 140 is formed from a preshaped or pliable, non-expanding material. Rectal probe 140 is configured such that rectum 26 properly adapts about probe 140 without requiring expansion of probe 140. Rectal probe 140 includes body 142, fluid lines 144A and 144B, electrical cable 146 and fluid lumens 148A–148D. Fluid lumens 148A–148D, which attach to fluid lines 144A and 144B, provide the identical cooling function which is accomplished through filling balloon 54 or by fluid lumens 138A–138F in FIGS. 3B and 4B, respectively. Specifically, fluid lumens 148A–148D provide rectal cooling during a therapy session.

The present invention provides an asymmetric heating pattern which is developed about urethra 10 during a transurethral microwave thermal therapy session which includes rectal cooling. Thus, a relatively large volume of tissue enveloping the anterior and lateral portions of prostate 14 can be heated to a temperature above about 45° C. which effectively necroses the tumorous tissue which encroaches upon urethra 10. In comparison, the temperature of tissue immediately anterior to rectum 26 and posterior to urethra 10 remains below about 42.5° C., thereby eliminating the harmful effects of the microwave heating to rectum 26 and adjacent tissue. The present system can be used with a variety of catheters which could include an antenna asymmetrically positioned within catheter 30 and/or asymmetric cooling within catheter 30 to provide the necessary asymmetrical heating pattern to necrose desired diseased tissue while protecting healthy tissue.

Although the present invention has been described with reference to preferred embodiments, workers skilled in the art will recognize that changes may be made in form and detail without departing from the spirit and scope of the invention.

What is claimed is:

1. A rectal probe apparatus comprising:
   a probe body selected from the group consisting of an inflatable balloon and a preshaped noninflatable body configured to conform to a rectal cavity, the probe body having a plurality of longitudinally extending lumens adjacent to one side of the probe body, the plurality of lumens having a cross-sectional area substantially less than that of the probe body; and
   means for providing a coolant to the plurality of lumens.

2. The apparatus of claim 1, wherein the means for providing a coolant comprises a fluid supply system connected to the probe body for supplying fluid to the plurality of cooling lumens.

3. The apparatus of claim 1, wherein the fluid supply system includes a temperature control system for controlling a temperature of the fluid supplied to the plurality of cooling lumens.

4. The apparatus of claim 1, wherein the probe body comprises an inflatable balloon having a wall, the wall having a thickness in the range of 0.005 to 0.100 inches.

5. The apparatus of claim 1, further comprising a temperature sensor positioned on the probe body for sensing a temperature of tissue adjacent to the probe body.

6. The apparatus of claim 1, wherein the probe body is composed of a thermally conductive material.

7. The apparatus of claim 1, wherein the probe body has sufficient torsional rigidity to permit positioning of the probe body within a rectum of a patient.

8. The apparatus of claim 1, further comprising a gas release means positioned within the probe body for releasing gas from a rectum of a patient.

9. A prostate treatment system comprising:

a rectal probe comprising an outer perimeter, a plurality of cooling lumens adjacent to the outer perimeter on a first side of the rectal probe, and means for providing a cooling fluid to the cooling lumens; and energy-delivering means located outside a rectum for providing microwave radiation to a prostate of a patient.

10. The prostate treatment system of claim 9, wherein the rectal probe comprises an inflatable balloon having an enlarged wall portion on a first side of the rectal probe, the plurality of cooling lumens extending longitudinally through the enlarged wall portion.

11. The prostate treatment system of claim 9, wherein the energy-delivering means is positioned within a urethra of the patient.

12. The prostate treatment system of claim 11, further comprising a temperature sensor positioned within the urethra of the patient for sensing a temperature within the urethra.

13. The prostate treatment system of claim 11, further comprising a transurethral temperature control system for controlling the energy-delivering means and thereby controlling a temperature of the urethra of the patient.

14. A method of treating a prostate of a patient, comprising:

inserting a rectal probe into a rectum of the patient, the rectal probe having a plurality of lumens adjacent to an outer perimeter thereof;

positioning the rectal probe within the rectum such that the outer perimeter of the rectal probe conforms to a rectal wall and the plurality of lumens are located adjacent to an anterior side of the rectum;

supplying a cooling fluid to the plurality of lumens adjacent to the outer perimeter of the rectal probe; and applying microwave radiation from a transurethral catheter to heat a portion of the prostate.

15. The method of claim 14, further comprising monitoring a temperature of the cooling fluid supplied to the plurality of lumens.

16. The method of claim 15, further comprising monitoring a temperature of tissue anterior to the rectum.

17. The method of claim 15, further comprising controlling a temperature of the cooling fluid supplied to the plurality of lumens.

18. The method of claim 15, further comprising controlling a power of the microwave radiation applied from the transurethral catheter to heat the prostate.

* * * * *